United States Patent [19]
Wilt et al.

[11] Patent Number: 6,087,662
[45] Date of Patent: Jul. 11, 2000

[54] PROCESS FOR ANALYSIS OF ASPHALTENE CONTENT IN HYDROCARBON MIXTURES BY MIDDLE INFRARED SPECTROSCOPY

[75] Inventors: Brian K. Wilt; William T. Welch, both of Ashland, Ky.

[73] Assignee: Marathon Ashland Petroleum LLC

[21] Appl. No.: 09/083,913

[22] Filed: May 22, 1998

[51] Int. Cl.[7] ............................ G01N 21/35; G01N 33/26
[52] U.S. Cl. .............................. 250/339.12; 250/339.09; 250/341.5; 436/60; 436/139
[58] Field of Search ........................... 250/339.09, 338.5, 250/339.01, 339.1, 339.11, 339.12, 341.5, 341.8; 436/52, 60, 139, 140, 141

[56] References Cited

U.S. PATENT DOCUMENTS

| | | |
|---|---|---|
| 4,940,900 | 7/1990 | Lambert . |
| 5,266,800 | 11/1993 | Mullins ................................... 250/256 |
| 5,452,232 | 9/1995 | Espinosa et al. . |
| 5,475,612 | 12/1995 | Espinosa et al. ........................ 364/500 |
| 5,672,873 | 9/1997 | Yamazoe ............................ 250/339.12 |
| 5,817,517 | 10/1998 | Perry et al. ............................... 436/55 |

*Primary Examiner*—Constantine Hannaher
*Assistant Examiner*—Albert Gagliardi
*Attorney, Agent, or Firm*—Laurence P. Hobbes; Richard D. Stone

[57] ABSTRACT

Asphaltene concentration of a hydrocarbon feed is measured by IR spectroscopy using mid-range IR frequencies between 3800 $cm^{-1}$ and 650 $cm^{-1}$ (corresponding to wavelengths between 2630 nanometers (nm) and 15,380 nm) together with mathematical techniques and statistical techniques in which measurements of absorption are made, and combines these with multiple regression analysis, or other statistical technique and modeling to determine asphaltene concentration. The output signal can be used to control refinery and chemical processes, e.g., atmospheric crude column, vacuum distillation column, solvent deasphalting and visbreaking.

19 Claims, 9 Drawing Sheets

PROCESS FOR ANALYSIS OF ASPHALTENE CONTENT IN HYDROCARBON MIXTURES BY MIDDLE INFRARED SPECTROSCOPY

Asphaltenes, defined as those components of a crude oil, fuel oil or distillation residue which are insoluble in heptane at its boiling point and soluble in benzene at its boiling point, are black to dark brown solids having a molecular structure of polynuclear aromatic rings with alkyl side chains and heteroatoms, such as nitrogen, oxygen, and sulfur attached. Asphaltenes can be indirectly measured by spectral analysis. U.S. Pat. No. 4,940,900 to Lambert discloses measurement of the flocculation threshold of a petroleum product containing asphaltenes by measuring the radiation in the near infrared transmitted through a sample of the product in solution in relation to the quantity of precipitant continuously added to the sample. The method requires addition of both a solvent and precipitant to the asphaltene-containing product tested.

U.S. Pat. No. 5,452,232 to Espinosa et al. (Example 19) discloses the determination of asphaltene content of a crude by obtaining near IR absorbance values (4640 $cm^{-1}$ to 4305 $cm^{-1}$) and correlating the absorbances using an equation.

Middle-IR (4000–650 $cm^{-1}$) has been used to determine the functional groups in asphaltenes by methyl ratio, paraffinic and naphthenic carbons, and alkyl side chain length.

The refining of heavier crudes in the coming decades poses problems to petroleum producers and refiners. During production, unwanted asphaltene precipitation causes well plugging; during refining, asphaltenes cause refinery heat exchanger fouling, as well as poisoning of catalysts by coking or binding of active sites with heavy metals. Moreover, sulfur found in crude oil asphaltene residual is unwanted in highly valued products such as gasoline and diesel fuel.

Accordingly, determining asphaltene content of petroleum by direct measurement, i.e., in the absence of added alkanes, would provide faster results than the methods currently used which require large amounts of solvent and can take several hours to perform.

The present invention utilizes a combination of selected mid-range IR frequencies between 3800 $cm^{-1}$ and 650 $cm^{-1}$ (corresponding to wavelengths between 2630 nanometers (nm) and 15,380 nm) together with mathematical techniques and statistical techniques in which measurements of absorption are made, and combines these with multiple regression analysis, or other statistical technique and modeling to determine asphaltene concentration.

Accordingly, the present invention relates to a process for determining asphaltene concentration in an asphaltene-containing hydrocarbon mixture using mid infrared spectroscopy and a multiple variable regression analysis to determine asphaltene concentration, comprising in combination:

a. measuring at at least one frequency, the middle infrared absorption in the band of 3800–700 $cm^{-1}$;

b. taking each of the absorbances measured, or a mathematical function thereof;

c. performing statistical treatment using the above absorbances or functions as individual independent variables;

d. assigning and applying weighting constants or their equivalents to said independent variables;

e. applying the above steps using compositions of known asphaltenes concentration to calibrate the instrument and determine said weighting constants or equivalents;

f. repeating said steps with unknown compositions, and applying the weighting constants or equivalents determined during said calibration with compositions of known asphaltenes concentration to output a signal or signals indicative of asphaltenes concentration for the unknown compositions.

The absorption can be measured over the entire length of the band of 3800–700 $cm^{-1}$, or of a portion thereof. In one embodiment, the absorption is only measured over the length of the band of 900–700 $cm^{-1}$, or of a portion thereof. In an especially preferred embodiment, the absorption is only measured at the frequencies of the bands of 1615–1300 $cm^{-1}$, 1100–1000 $cm^{-1}$ and 975–700 $cm^{-1}$, or of portions thereof.

The direct measurement techniques of the present invention can be applied to asphaltene-containing petroleum streams such as desalted crude oil and other refinery streams, including atmospheric distillation bottom feeds, residuals, crude unit vacuum bottom feeds, pipelined crude oil, and solvent deasphalting bottoms product.

The signal obtained in accordance with the present invention can be used to control the severity of an atmospheric or vacuum distillation column by adjusting cut point, temperature, throughput, and/or unit space velocity. Alternatively, the signal can be used to control the severity of a solvent deasphalting unit by adjusting temperature, throughput, unit space velocity and/or alkane solvent to vacuum bottoms ratio. In yet another embodiment, the signal is used to control the severity of a visbreaker by adjusting temperature, throughput, and/or unit space velocity.

The method of the present invention may be used to control and optimize petroleum processing operations off-line in the laboratory or on-line if the measuring system is used directly for process control. The invention may also be used to control and correct the stability of fuel oils and to control the transporting of crude petroleum products in pipelines by determining the characteristics of blends carried. The present invention method can be used to control a distillation column for example by control of upstream heaters. In another aspect of the invention, the measurement technique of the present invention can be used to control a solvent deasphalter in order to provide a deasphalted product having a set concentration of asphaltene.

DETAILED DESCRIPTION

The hydrocarbon compositions may flow substantially intermittently or continuously past the point where the measurements are being made.

Signal Processing:

The absorbance signal from the measurement of the characteristic hydrocarbon species bands, used either solely or in conjunction with other bands, will preferably be mathematically processed to provide derived signals which are indicative of the concentrations (or property) being measured. Preferred techniques for mathematical processing are absorbance base line off-set corrected absorbance data; taking the first, second, third, fourth or higher derivative of the absorbance spectrum; the technique of dividing the absorbance at one wavelength by another; spectral subtraction; and various combinations of these mathematical techniques. Also valuable are the well-known curve fitting techniques of Savitsky-Golay and Kubelka-Munk, and N-point smoothing (signal averaging). Other types of statistical data treatment comprise principle component analysis/regression (PCA/PCR), partial least squares (PLS), Gauss-Jordan Row reduction, etc. In these techniques, correlations are found among the constituent values of interest and one or more mathematically determined equivalent weighting constants. PLS is especially preferred.

By equivalent weighting constant we mean to include, among other mathematical constructions known to the art, the wavelength coefficients of multiple linear regression, the factors of partial least squares regression, the scores of principal component regression, or the constants obtained from the Gauss-Jordan Row reduction algorithm. (See Harald Martens and Tormod Naes, Multivariate Calibration, John Wiley & Sons; New York, 1989 [ISBN 471-90979-3], and Honigs, D. E., Heiftje, G. M.; Hirschfeld, T., Applied Spectroscopy, 38(3), 1984, p. 317.) Also any constant obtained from any statistical calibration could be used to calculate values for unknown samples. The present Example uses partial least squares.

This invention will find its greatest application in the petroleum refining industry and can be used to monitor the amounts of asphaltene in a crude feed to and from a distillation column, visbreaker, or solvent deasphalter.

A multiplexed or multistreamed on-line middle IR can be configured so that the feed and product asphaltene contents can be determined by a single IR which alternates between the feed and product streams. The feed forward IR can determine the purity of the feed and predict parameters such as the optimum temperature, throughput, and/or unit space velocity.

The invention will find many applications of hydrocarbon species analysis outside of the petroleum industry, including coal mining.

Analytical Equipment:

Middle infrared (MIR) spectrometers, Fourier Transform middle infrared (FTMIR) spectrometers, and modified middle infrared spectrometers of conventional design may be used with the invention. Preferred modes of operation are transmission, reflectance, and transflectance. More preferred is reflectance. Most preferred is Attenuated Total Reflectance (ATR). Suitable spectrometers are the Analect Diamond-20 spectrometer with a spectral range from 7000 cm$^{-1}$ to 400 cm$^{-1}$ available from Analect of Irvine, Calif. The spectrometer can be operated in a quality control lab, on a batch basis (receiving signals, e.g., by a sample feeding arrangement), or, more preferably, on a continuous basis in which the fluid to be measured flows through a cell or in which a probe immersed in the flowing fluid transmits optically through a fiber-optic cable to the spectrophotometer. The techniques for sampling, measuring, and signal processing can be conventional and are well known to those skilled in the art.

Figure 1:
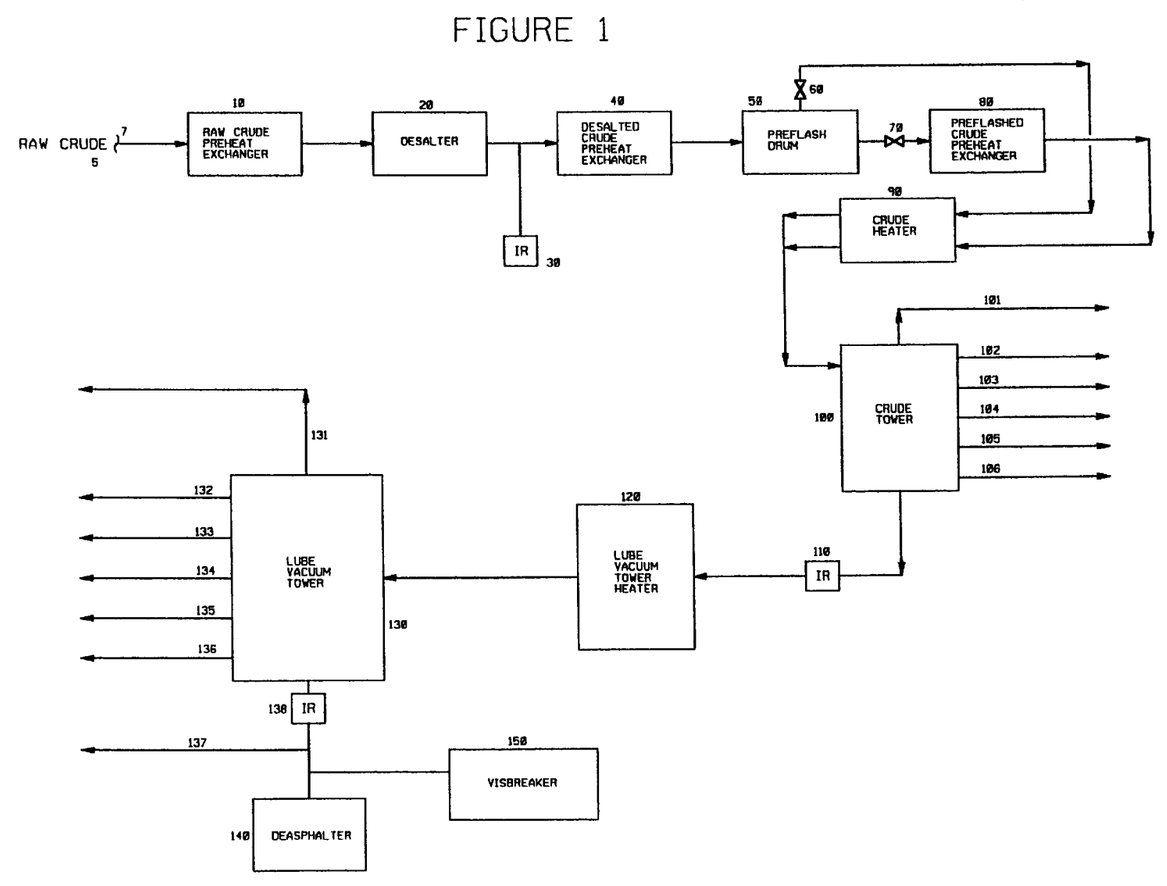
FIG. 1 is a plot of a typical refinery scheme comprising an atmospheric crude column, lube vacuum tower, solvent deasphalter and visbreaker with the preferred middle infrared spectrometers of the present invention used to control temperature, throughput, unit space velocity, and/or alkane solvent/vacuum bottoms ratio via feed-forward and/or feedback, middle-infrared control.

(Invention Controlling a Crude Column, Vacuum Column, Solvent Deasphalter and Visbreaker)

FIG. 1 shows schematically the process flow of a typical refinery having atmospheric and lube vacuum towers. Raw crude 5 is passed by crude pump 7 to raw crude preheat exchangers 10 and thence to desalter 20. An IR cell 30 placed between desalter 20 and desalted crude preheat exchanger 40 measures asphaltene concentration of the desalted feed and by feed forward and/or feedback control adjusts feed space velocity, e.g., by controlling crude pump 7, and/or feed temperature, e.g., by controlling raw crude preheat exchangers 10, desalted crude preheat exchangers 40, and/or preflashed crude preheat exchangers 80. The feed thence passes to a preflash drum 50 where it is routed by valves 60 and 70 to preflashed crude preheat exchangers 80 and thence to crude heater 90 or directly to crude heater 90. The feed passes from crude heater 90 to atmospheric crude tower 100 where gas is taken off at 101 as overhead to a saturated gas plant or flared, distillate is taken off the column as Light Straight Run (LSRN) to Light Ends Processing (LEP) at 102, Heavy Straight Run (HSRN) to reformer at 103, kerosene to storage at 104, diesel to storage at 105, and heavy gas oil (HGO) to FCC at 106. The atmospheric resid is passed (optionally through IR analyzer 110 wherein asphaltene concentration is measured and said measurement used to adjust throughput and/or heat downstream) to lube vacuum tower heater 120 and thence to lube vacuum tower 130 wherein the tail gas is taken off at 131 as overhead and cycled to lube vacuum tower heater 120, vacuum distillate is taken off the column as light vacuum gas oil (LVGO) to FCC at 132, 100 N distillate to the lube plant at 133, 300 N distillate to the lube plant at 134, heavy vacuum gas oil (HVGO) to an RCC® heavy oil conversion process as taught in U.S. Pat. Nos. 4,347,122; 4,341,624; 4,414,098; 4,431,515; and 4,444,651 at 135, and cylinder stock to RCC® at 136. The vacuum bottoms are taken off at 137 and passed to asphalt oxidizer or mixed with fuel oil. The vacuum bottoms may alternately be passed to a solvent deasphalter 140 wherein conditions such as alkane solvent to vacuum bottoms ratio, temperature, throughput, and the like are controlled according to asphaltene content as measured by MIR cell 138 which measures asphaltene content of the vacuum bottoms. The vacuum bottoms may also be directed to visbreaker 150 which can also be controlled by the MIR cell at 138. Vacuum bottoms may also be passed to visbreaker whose temperature and throughput can also be controlled according to asphaltene content of the vacuum bottoms as measured by MIR cell 138.

MIR analyzer 30 samples the effluent from the desalter, and analyzes it for asphaltene content in accordance with the present invention technique. The greater the asphaltene content, the lower the temperature of the various heaters upstream of the atmospheric crude column, or the greater the throughput of crude so as to increase space velocity to the column so as to prevent entraining asphaltene in the distillate product.

According to the invention, a mid-infrared (MIR) instrument 30 with closed-loop control capability and operating according to the techniques described above, is placed "at line" so that it measures a portion of the desalter product, and analyzes it for asphaltene content. Noting any differences between the measured value and the desired value, the MIR closed-loop control unit 140 sends a signal to one or more of the heaters, e.g., 90 and/or 120, or heaters for solvent deasphalter 140 or visbreaker 150 to increase or decrease their temperature. By increasing the temperature of the visbreaker and/or decreasing space velocity or throughput of feed, the "severity" of the visbreaking process is increased which tends to increase the likelihood that the asphaltene will precipitate out of the visbroken resid due to the overcracking of heavy hydrocarbon oils to lower boiling compounds, some of which are removed thus increasing the asphaltene concentration. By measuring asphaltene content of the feed to the visbreaker, reaction conditions can be moderated when asphaltene content is higher, and made more severe when asphaltene content is lower.

Additionally, or alternatively, the MIR instruments 30, 110, and 138 (or the same MIR instrument 30 multiplexed for either multistreaming or multiplexing with fiber optics so as to analyze desalter effluent, crude tower 106 effluent and lube vacuum tower 138 effluent), measure the various effluents and by "feed forward" predicts the temperature and throughput needed for the heaters and pumps in order to provide the desired product slate.

The invention controls the product characteristics more closely than the similar method employing NIR because the MIR instrument provides more well-defined spectra with less overlap than NIR.

EXAMPLE

Fifty raw crude oil samples were collected for use in asphaltene calibration and prediction sets. The oils had origins from a wide array of geochemical conditions from around the world.

Vacuum distillations were performed to produce different boiling range fractions of each crude. The heavy end boiling fractions from the crudes with boiling points >900° F. (482° C.) were saved in small round metal cups and covered with aluminum foil. The heavy fractions from three oils were used in an experiment to determine the infrared absorbance bands for the asphaltenes.

The asphaltene content of the fifty crude oils and their heavy boiling fractions were determined using a modified ASTM method D-4055. First, a liter bottle of crude was mixed well by shaking vigorously by hand for one minute. Approximately 5 g of the crude oil was transferred using a disposable polyethylene pipet into a 300 ml Pyrex® fleaker (Corning). The weight of the crude added to the fleaker was determined using a Mettler AT200 balance and recorded. Next, 200 ml of reagent grade n-pentane was added to the fleaker. The fleaker was capped and placed into a 2120 Branson sonication bath, available from Branson Ultrasonic, Inc. of Danbury, Conn., for 30 minutes. After sonication, the precipitated asphaltene was recovered by filtering the sample through a previously weighed Whatman® 1.5 $\mu$m borosilicate filter using n-pentane to wash the asphaltenes from the sides of the fleaker several times to complete the transfer. Once the transfer was complete, the filter containing the asphaltene was placed in a vacuum oven for 30 minutes to evaporate any remaining n-pentane. The filter was removed from the oven and allowed to cool before reweighing. The total amount of time to deasphalt an oil was approximately 2.5 hours.

The deasphalted oil fractions from five selected crudes were recovered using a Buchi model 110 Rotovap. The deasphalted oil/pentane mixture was suctioned through a condensing column into a 250 ml round bottom boiling flask that was rotating in an 80° C. water bath. The n-pentane was boiled into the condensing column and was recovered in a 500 ml flask atached on a side arm of the condensing column. The recovered oil in the boiling flask was transferred and stored in 25 ml glass vials with polypropylene sealed caps.

Spectra of the 50 crude oils were collected on an Analect Diamond-20 spectrometer with a spectral range from 7000 $cm^{-1}$ to 400 $cm^{-1}$. Only the mid-IR spectral range of 4000 $cm^{-1}$ to 650 $cm^{-1}$ was used. Spectra were an accumulation of 128 scans with a spectral resolution of 4 $cm^{-1}$. The time to acquire all 128 scans was approximately 150 seconds. The infrared radiation was measured using a deuterated triglycine sulfate (DTGS) detector. The data system employed to control the instrument consisted of a Dell 486DX CPU with an arithmetic coprocessor and the instrument manufacturer's data collection software.

Two types of infrared sample cells were used in the experiment including NaCl plates (International Crystal Laboratories) and a Tunnel® ATR Cell from Axiom Analytical of Irvine, Calif. The Tunnel® cell contained a zinc selenide element with a diameter of 3.2 mm, and a length of 40 mm. The number of effective internal reflections through the prism was 10 with a total flow volume of 40 microliters.

Five crudes having differing amounts of asphaltenes were selected to see if infrared absorption bands for the asphaltenes were common to all samples. Crude oils selected included a Eugene Island (EIC), a Maya (MYA), a Statfjord (STF), a Mesa 30 (MES) and a Cetex (CTX). Once the asphaltene content for each was determined, the asphaltene fraction and the deasphalted oil fraction for each crude were retained for FR-IR analysis. Heavy end boiling fractions from three crudes (EIC, STF, and CTX) were deasphalted to obtain enough asphaltene to analyze by FT-IR.

A small amount of the asphaltene was transferred from the filter paper to a 15 ml Pyrex® beaker and dissolved with about 5 ml of 99.9% spectrophotometric grade carbon tetrachloride (Aldrich Chemical of Milwaukee, Wis. Two clean 25 mm×2 mm NaCl salt plates (International Crystal Laboratories of Garfield, N.J.) were assembled in a holder and placed in the Analect Diamond-20 to obtain a background spectrum. After completion, the NaCl plates were disassembled and placed face up on a hot plate on low heat. A polyethylene transfer pipet was used to drop the asphaltene/$CCl_4$ mixture onto the center of the heated NaCl plates evaporating the $CCl_4$ and leaving the asphaltene. After a sufficient amount of asphaltene was deposited on the plates, they were put in a vacuum oven at 160° C. for 15 minutes. After having been removed from the oven, the plates were allowed to cool in a desiccator before being reassembled in the holder, then placed back in the instrument to obtain the FT-IR spectra. Spectra of the deasphalted oil fraction were obtained in the same manner except that heating the NaCl plates on the hot plate was not necessary because the oil was placed directly on the plates and no carbon tetrachloride needed to be evaporated.

Spectra were also acquired on a 50% asphaltene/50% deasphalted oil mixture of each of the five selected crudes to help in verifying the asphaltene absorption bands. The samples were prepared by weighing 0.1 g of the asphaltene into a 15 ml beaker, then adding 0.1 g of the deasphalted oil. Five ml of carbon tetrachloride were added to the beaker to fully dissolve the asphaltene. The sample was mixed thoroughly with a glass stirring rod then deposited using a transfer pipet on heated salt plates to evaporate the $CCl_4$. The plates were placed in the vacuum oven, then allowed to cool before FT-IR spectra were obtained.

Samples of the 50 crude oils were shaken vigorously and poured into 15 ml beakers. The oil was introduced into the cell using 20 ml disposable syringes. Approximately 10 cm of poly(tetrafluoroethylene) (PTFE) tubing was used to connect the syringe port to the inlet of the Tunnel® cell. Thus the sample compartment did not have to be opened to inject the crude oil sample. PTFE tubing was also used to connect the outlet of the cell to a 1000 ml Erlenmeyer flask used as a waste collection reservoir. The cell was cleaned between oil samples with 50 ml of toluene followed by 50 ml of n-pentane. The pentane was evaporated from the cell by purging for five minutes with air supplied from a Balston purge gas generator. The technique was repeated for all fifty crude oil samples.

All collected spectra were imported into Galactics' Grams 386 software obtained from Galactic Industries for multivariate regression analysis.

The FT-IR asphaltene absorption bands were determined by analyzing the asphaltene fraction, the deasphalted oil (DAO), and a 50% asphaltene/50% DAO sample for each of five crude oils—MES, MYA, EIC, CTX, STF-used in the calibration set. The asphaltene content for the five oil samples ranged from 0.50 to 14.93 wt. %. Each crude in this set was deasphalted three times to test the repeatability of the test method. The average asphaltene contents and the corresponding standard deviations for each crude was determined to be as follows: MES 3.34+/−0.13 wt. %, MYA 14.93+/−0.42 wt. %, EIC 1.61+/−0.15 wt %, CTX 8.49+/−0.21 Wt %, and STF 0.50+/−0.08 wt %. The repeatability limit of the ASTM method at 95% confidence limits is dependent upon the amount of asphaltene present in the oil and is defined by the following equation: Repeatability is equal to $0.177((2/3)x)$ where x is the average asphaltene value. All samples except the STF crude are within the repeatability limits. The repeatability of the STF is slightly greater than the method.

Figure 2:
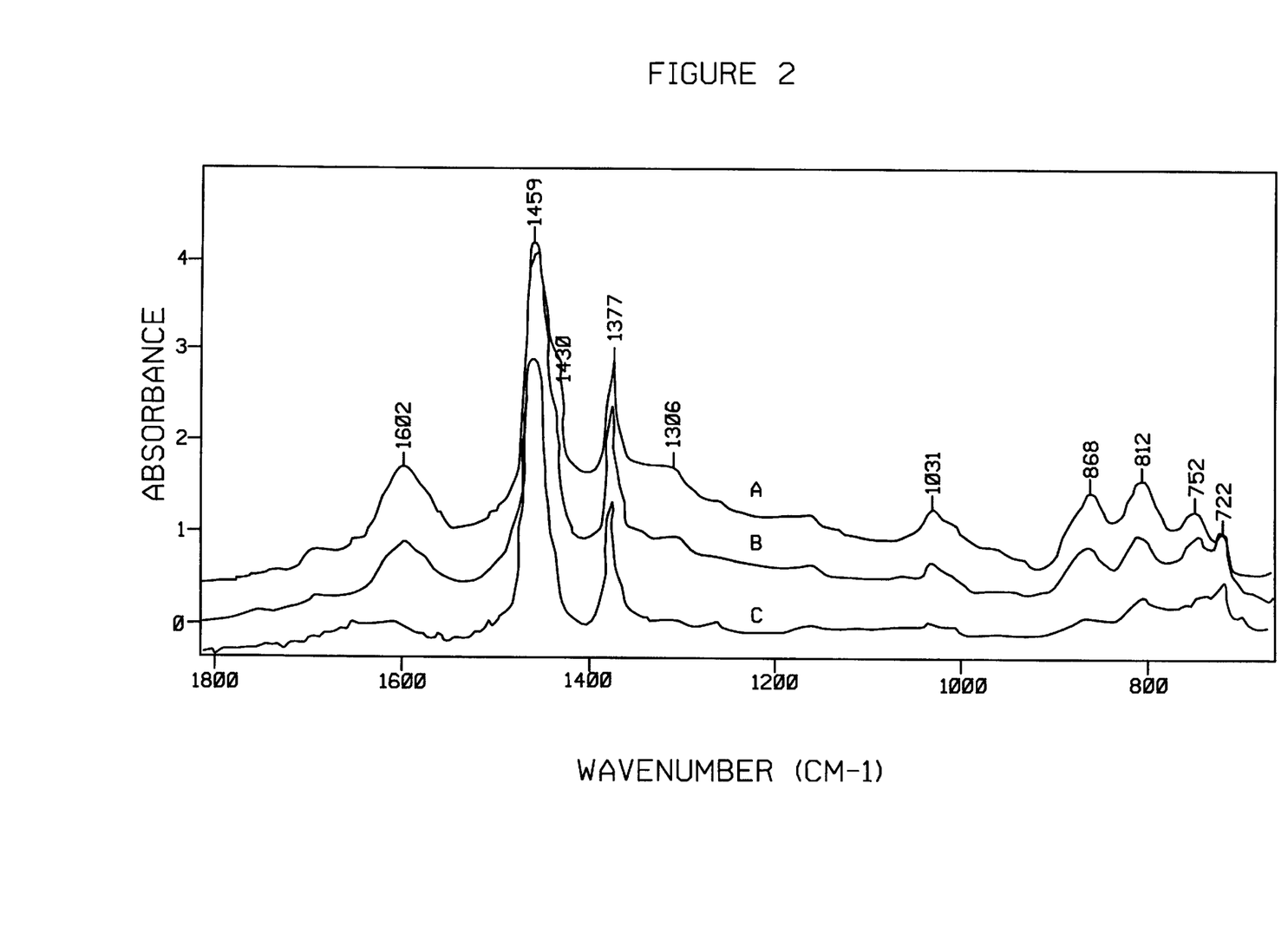
FIG. 2 is a plot of the FT-IR spectrum of a CTX stream (Cetex) of crude oil from 1800 $cm^{-1}$ to 680 $cm^{-1}$ showing (A) 100% asphaltene, (B) 50% ASP/50% DAO, and (C) 100% DAO.
Figure 3:
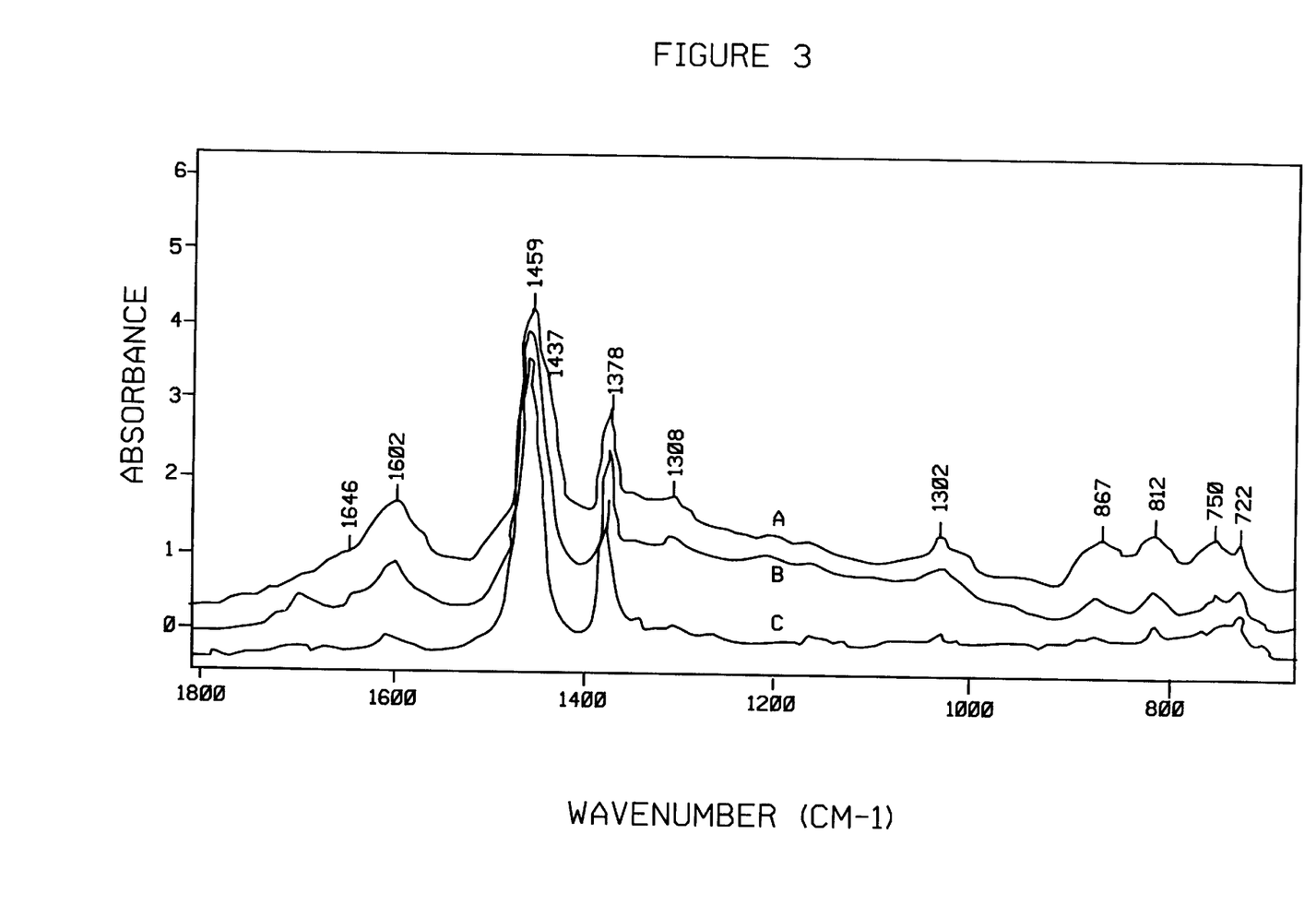
FIG. 3 is a plot of the FT-IR spectrum of an EIC (Eugene Island) crude oil from 1800 $cm^{-1}$ to 680 $cm^{-1}$ showing (A) 100% asphaltene, (B) 50% ASP/50% DAO, and (C) 100% DAO.

Referring now to the drawings, in FIGS. 2 and 3, a series of FT-IR spectra of the fraction from CTX (FIG. 2) and EIC (FIG. 3), crude is presented. There are absorbance bands in the asphaltene spectrum (A) that are not present in the DAO spectrum (C). These areas include a peak located at 1602 $cm^{-1}$, a shoulder centered near 1435 $cm^{-1}$, and peaks at 1306 $cm^{-1}$, 1032 $cm^{-1}$, 868 $cm^{-1}$, 812 $cm^{-1}$, 752 $cm^{-1}$, and 722 $cm^{-1}$. It is important to note that the same peaks are observed for both crude oils even though the asphaltene concentrations of the two crudes were determined to be very different (1.6 wt % and 8.5 wt %) and the oils formed under different geological conditions. Spectra collected on the fractions of the remaining three crudes were typical of the spectra presented in FIGS. 2 and 3.

Functional groups present in the asphaltene and 50/50 mixture fractions can be identified and assigned from the literature. The broad peak at 1602 $cm^{-1}$ corresponds to the aromatic C=C stretching vibrations. The absorbances at 1459 $cm^{-1}$ and 1435 $cm^{-1}$ were due mainly to $CH_2$ bending modes with some contribution from $CH_3$ bending modes. Methyl bending vibrations were responsible for the peak at 1377 $cm^{-1}$. The sharp peak located at 1306 $cm^{-1}$ was due to the presence of ethers, or esters. The peak near 1032 $cm^{-1}$ can be assigned to ester linkages present in the asphaltene molecule. The four absorbances observed between 870 $cm^{-1}$ and 722 $cm^{-1}$ can be assigned to the aromatic CH out-of-plane bending vibrations. The number of hydrogen atoms adjacent to the CH bond causes four peaks to be observed.

Figure 4:
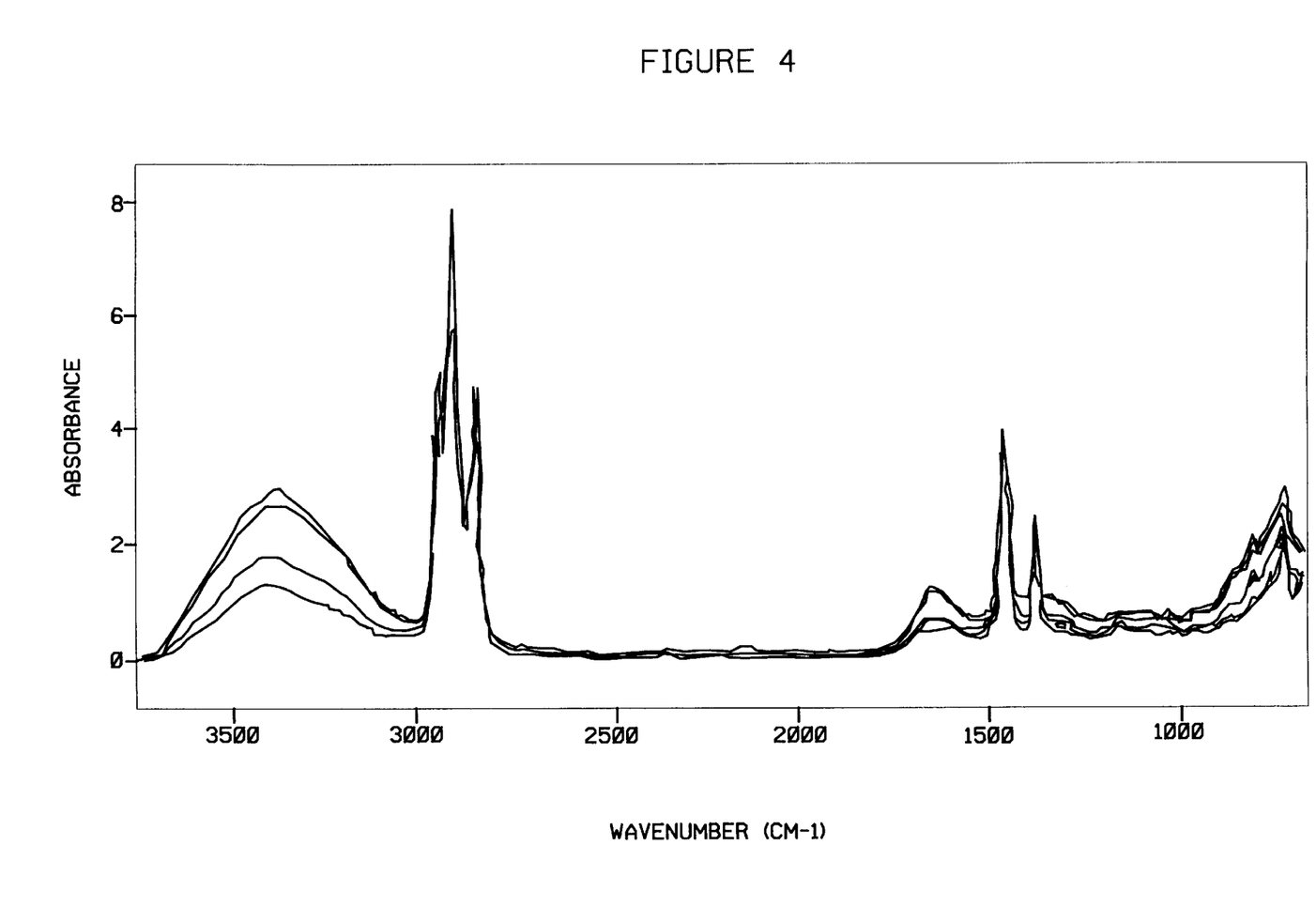
FIG. 4 is a plot of the FT-IR spectrum of five selected crude oils CRP (Caripito Pedernales), MYA (Mayan), KUW (Kuwait Export Blend), ABL (Arabian Light), and CUS (Cusiana) from 3700 $cm^{-1}$ to 680 $cm^{-1}$.
Figure 5:
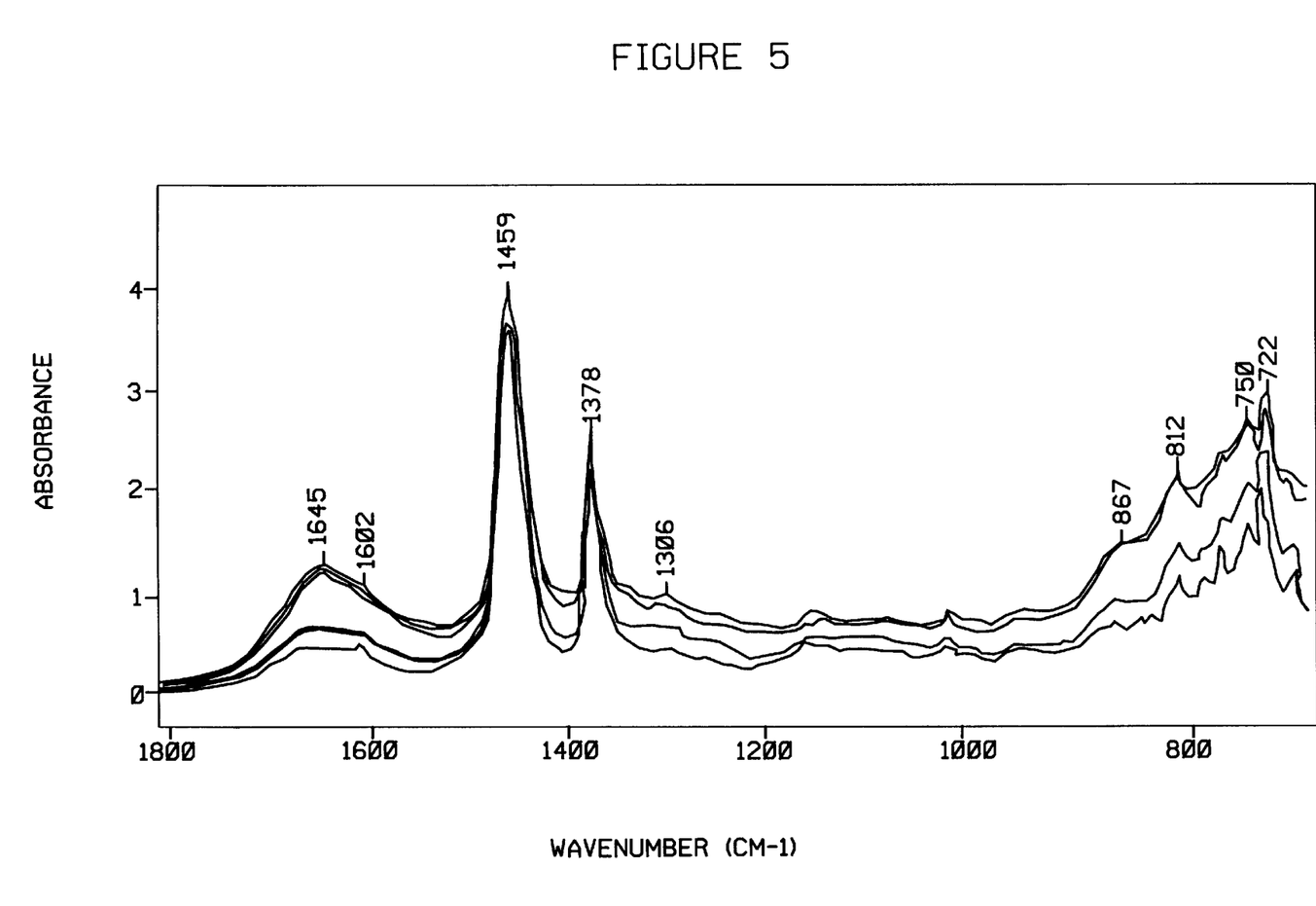
FIG. 5 is a plot of the FT-IR spectrum of five selected crude oils CRP (Caripito Pedernales), MYA (Mayan), KUW (Kuwait Export Blend), ABL (Arabian Light), and CUS (Cusiana) in the fingerprint region from 1400 cm$^{-1}$ to 680 cm$^{-1}$.

The spectra of five crude oils CRP, MYA, ABL, KUW, and CUS analyzed using the Tunnel cell are presented in FIGS. 4 and 5. The five oils had a range of asphaltene concentration from 0.8 wt. % to 14.55 wt. %. As can be seen from the spectra, some of the crudes contained large amounts of water, characterized by the large broad band at 3450 $cm^{-1}$. Absorbances found in the region from 1800 $cm^{-1}$ to 700 $cm^{-1}$ show many of the same characteristics of the spectra of the fractions shown in FIGS. 2 and 3. The peaks include a shoulder at 1602 $cm^{-1}$, the $CH_2$ and $CH_3$ bending vibrations between 1500 $cm^{-1}$ and 1350 $cm^{-1}$. A peak is observed at 1306 $cm^{-1}$ in the area of the bending vibrations of ethers or esters. The aromatic bending vibrations are also observed between 900 $cm^{-1}$ and 700 $cm^{-1}$.

Once the spectra had been collected, the spectra were imported into Grams®386 multivariate analysis software to regress against the asphaltene content determined by the n-pentane solvent method. The data set was divided into a calibration set of 42 samples and a prediction set of eight crude oils. The prediction set was used as a set of unknowns to test the validity of the model generated. The crude oil spectra used in the calibration were mean centered in the PLS Plus Chemometrics regression package (available from Galactic) before the regression was carried out. Leave one out cross validation was used to test the model. In this validation, each spectrum in the calibration set was left out then predicted from a model using all the other samples to test for concentration outliers. Several PLS modes were developed using different spectral regions to determine if the absorbance bands identified for asphaltenes gave the best results. In the Table below, the results of the PLS modeling are summarized.

TABLE

PLS PARAMETERS AND STATISTICS
FOR DETERMINATION OF ASPHALTENES IN CRUDE OIL

| Model No. | Wavelength Regions Used ($cm^{-1}$) | No. of Samples | Factors Used | $R^2$ | SEE (Wt. % Asp.) |
|---|---|---|---|---|---|
| 1 | 1615–1300, 1100–1000, 975–700 | 42 | 8 | 0.9495 | 0.92 |
| 2 | 4000–700 | 42 | 6 | 0.9016 | 1.31 |
| 3 | 900–700 | 42 | 6 | 0.9260 | 1.15 |

Figure 6:
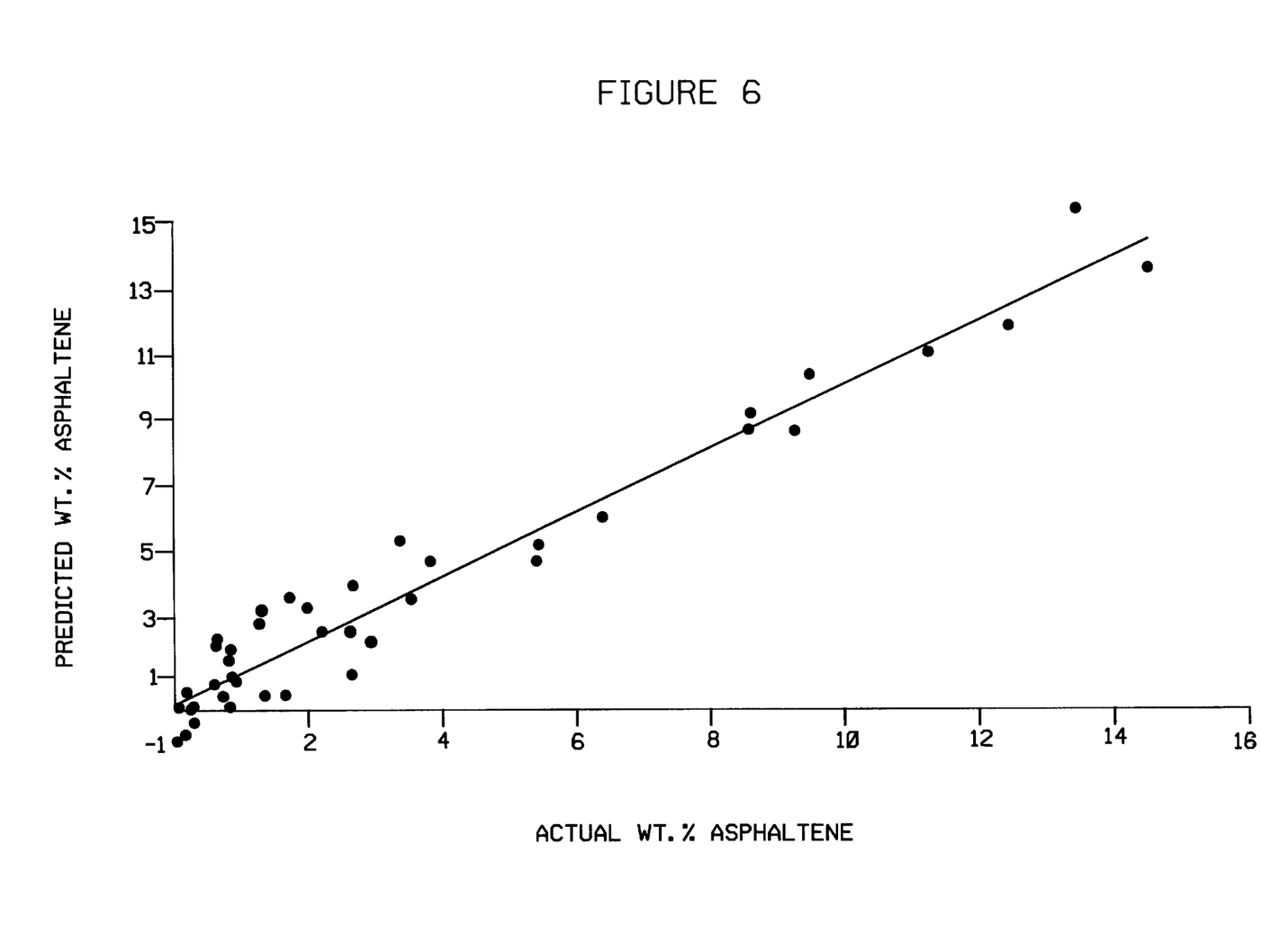
FIG. 6 is a plot of predicted asphaltene content versus actual asphaltene content for crude oil samples used in the calibration set.
Figure 7:
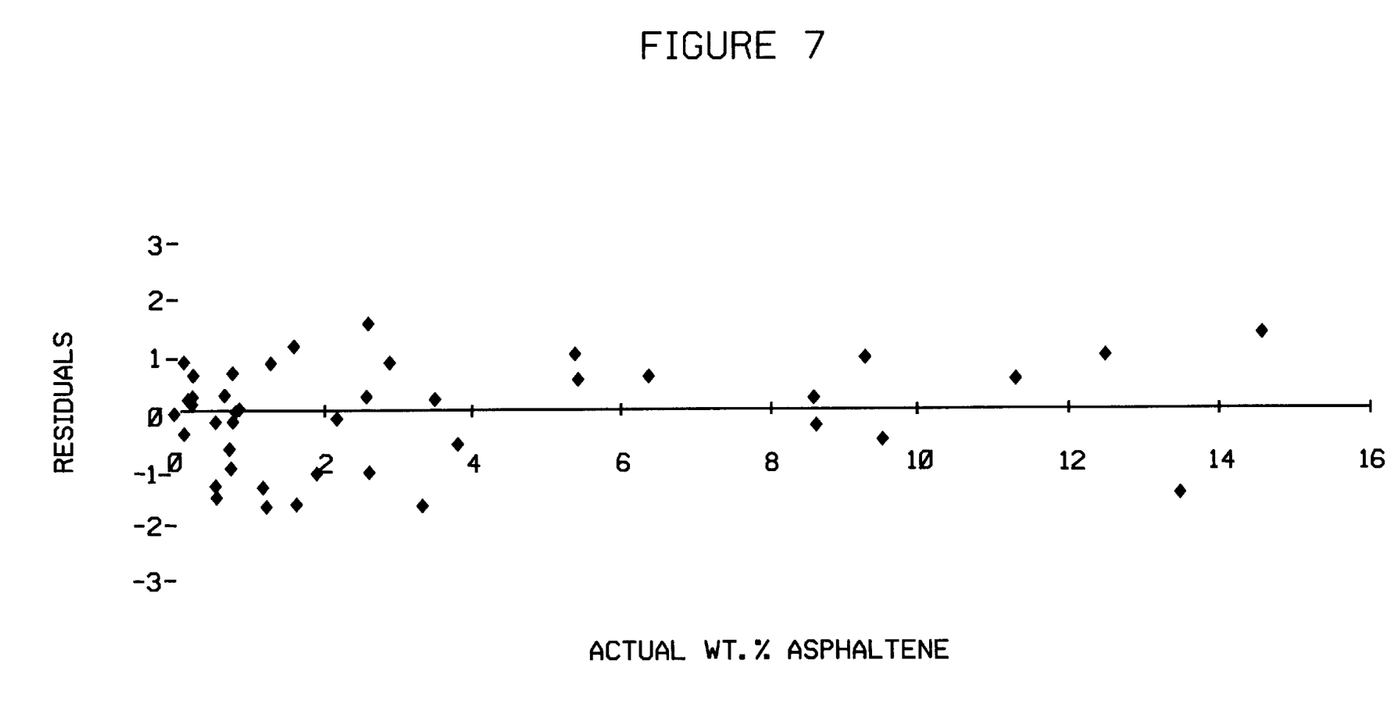
FIG. 7 is a plot of the absolute residuals (difference between predicted asphaltene content and actual asphaltene content) versus actual asphaltene content for the crude oil samples used in the sample set.

The Table shows model 1 is constructed from absorbance bands previously assigned to the asphaltene present in the crude oil. This model has a better $R^2$ and Standard Error of Estimate (SEE) than the other two models. FIG. 6 is a plot of the FT-IR predicted asphaltene value using model 1 versus the actual wt. % asphaltene content as determined by the n-pentane solvent method. There is a linear relationship between the two results. From the residual plot (FIG. 7) which compares the difference between predicted and actual asphaltene content versus actual asphaltene content, it is shown the absolute error is constant across the entire range of asphaltene concentration.

Model 2 was built using all wavelengths in the mid-IR region. This model is shown to have the worst SEE of the three. Model 3 was generated using only those bands assigned to the aromatic out-of-plane bending vibrations and, while producing better results than model 2, was still inferior to model 1. This indicates that the oxygen functional groups are important in determining the amount of asphaltene present in the crude oil. The error is determined to approximately +/±1 wt. % asphaltene.

Figure 8:
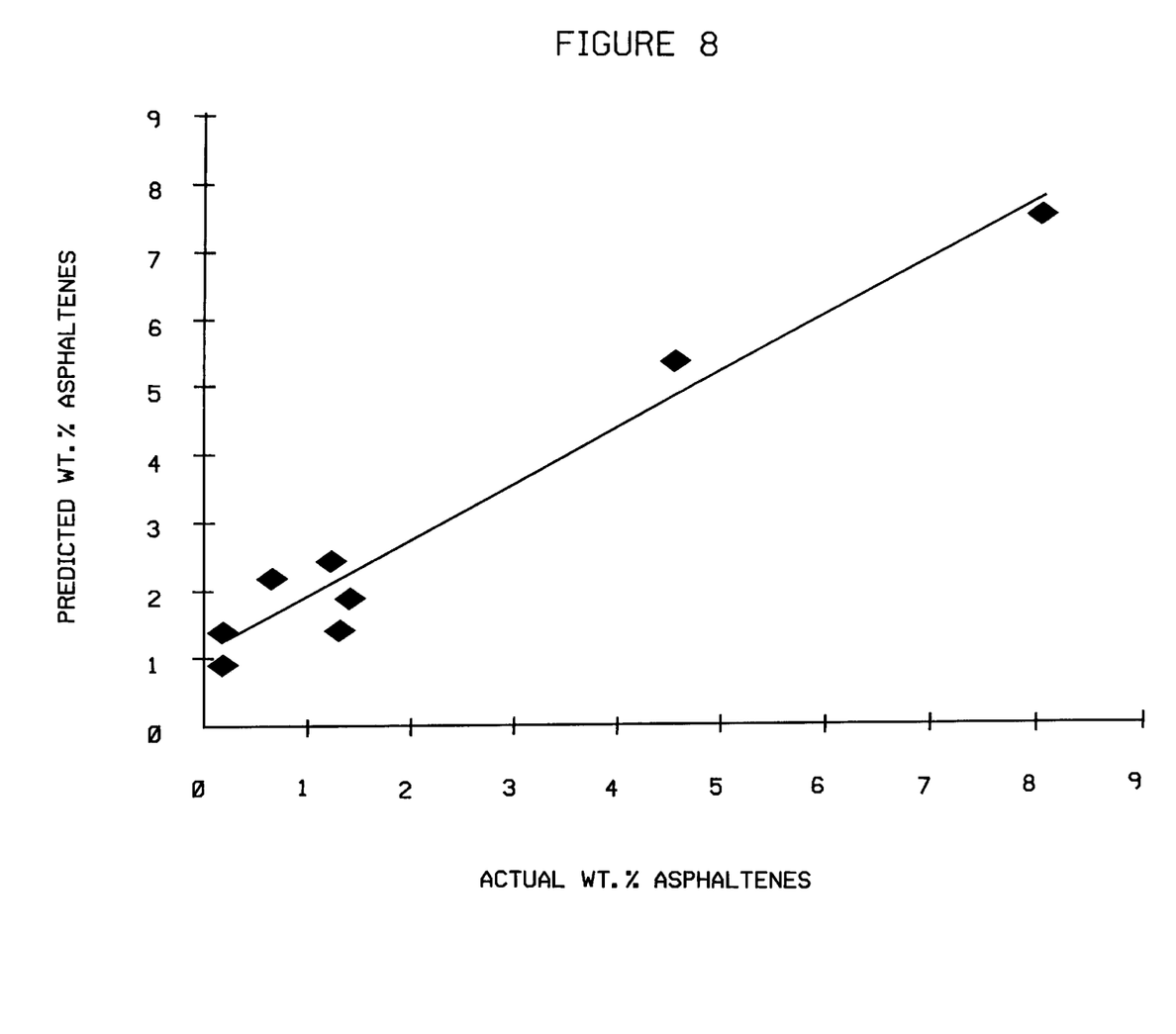
FIG. 8 is a plot of predicted asphaltene versus actual asphaltene content for a prediction set of eight crude oils.
Figure 9:
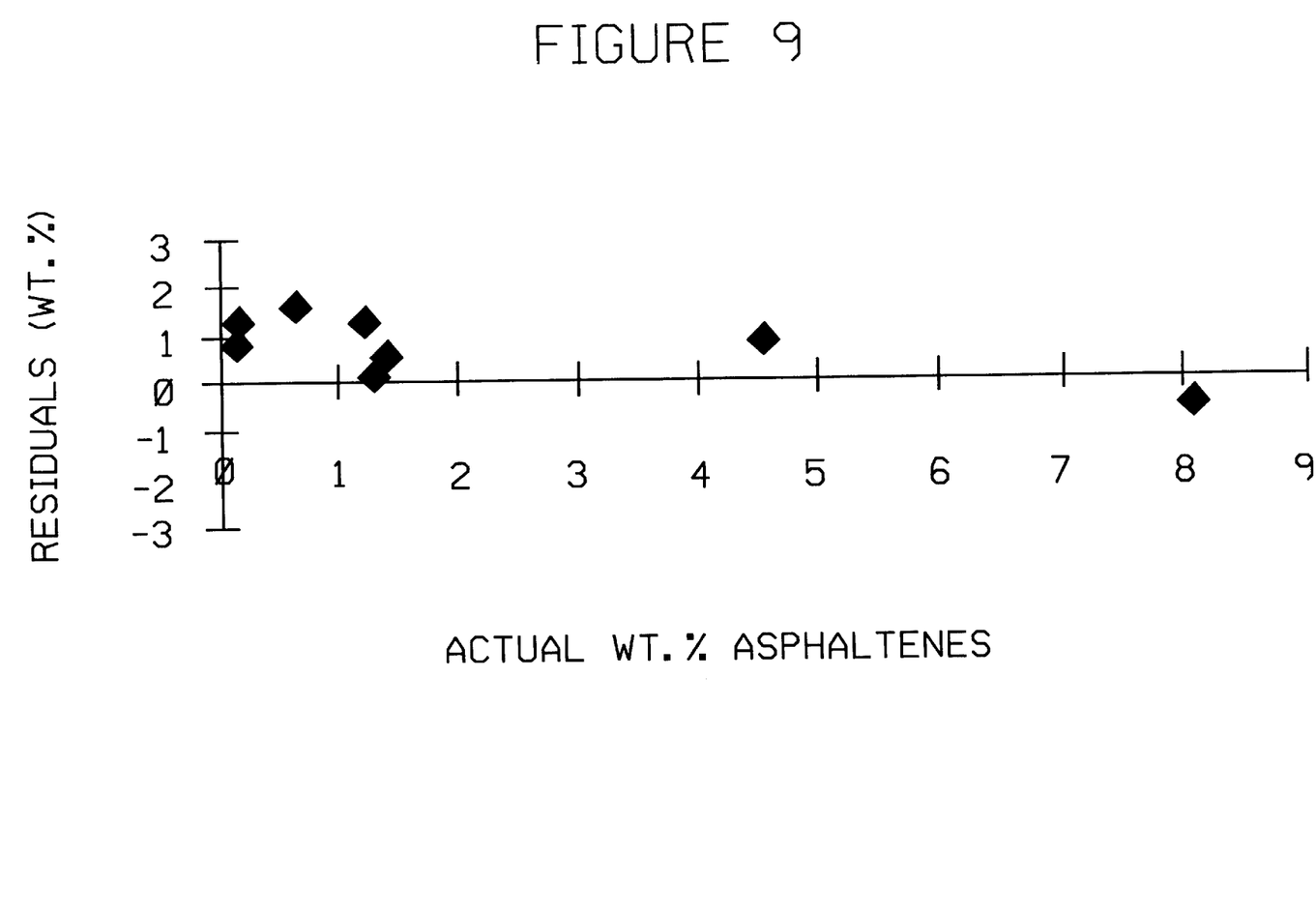
FIG. 9 is a plot of the absolute residuals versus actual asphaltene content for the prediction set of eight crude oils.

A second set of eight crude oils was used as a prediction set to test the validity of the calibration. The eight crudes Mixed Blend Sweet (MSW), Bow River (BOW), Penn Grade (Peake Energy) (PGP), Penn Grade (Eureka) PGE, Guafita (GUA), Olmeca (OLM), North Dakota Light (NDL), and North Louisiana Sweet (NLS) were selected at random. The prediction plot of these eight crudes is presented in FIG. 8. The $R^2$ value for the plot is 0.956 with a standard error of prediction (SEP) of 0.99 wt. %. Although a linear relationship exists between the predicted and actual wt. % asphaltene values, the residual plot (FIG. 9) shows a bias in the predictions of the crudes containing lower amounts of asphaltenes. Reasons for this may be first, that two samples containing lower amounts of asphaltenes (PGP, PGE) are Pennsylvania grade crude oils. Because this type of crude was not present in the calibration model, predicting such a crude may lead to the observed bias. Second, the eight samples were analyzed at a later date, which could have lead to slight changes in the instrument. The residual results of FIG. 9 are still comparable to the 1 wt. % residuals observed for the calibration set residuals of FIG. 7. Third, the validation set is small, and the predicted values are still within the results from the calibration set for samples at lower asphaltene concentrations.

What is claimed is:

1. A process for determining asphaltene concentration in an asphaltene-containing hydrocarbon mixture using infrared spectroscopy and a multiple variable regression analysis to determine asphaltene concentration, comprising in combination:
   a. measuring at at least one frequency, the infrared absorption in the band of 3800–700 $cm^{-1}$;
   b. taking each of the absorbances measured, or a mathematical function thereof;
   c. performing statistical treatment using the above absorbances or to functions as individual independent variables;
   d. assigning and applying weighting constants or their equivalents to said independent variables;
   e. applying the above steps using compositions of known asphaltenes concentration to calibrate the instrument and determine said weighting constants or equivalents;
   f. repeating said steps with unknown compositions, and applying the weighting constants or equivalents determined during said calibration with compositions of known asphaltenes concentration to output a signal or signals indicative of asphaltenes concentration for the unknown compositions.

2. The process according to claim 1 wherein absorption is measured over the length of the band of 3800–700 $cm^{-1}$, or of a portion thereof.

3. The process according to claim 1 wherein absorption is only measured over the length of the band of 900–700 $cm^{-1}$, or of a portion thereof.

4. The process according to claim 1 wherein absorption is only measured at the frequencies of the bands of 1615–1300 $cm^{-1}$, 1100–1000 $cm^{-1}$ and 975–700 $cm^{-1}$, or of a portion thereof.

5. The process according to claim 1 wherein said statistical treatment is a technique selected from the group consisting of absorbance base line off-set corrected absorbance data; taking the first, second, third, fourth or higher derivative of the absorbance spectrum; dividing the absorbance at one wavelength by another; spectral subtraction; curve fitting techniques of Savitsky-Golay; curve fitting techniques of Kubelka-Munk; N-point smoothing (signal averaging); principle component analysis/regression (PCA/PCR); Gauss-Jordan Row reduction; multiple linear regression analysis (MLR); partial least squares analysis (PLS); and Neural Networks (NN).

6. The process according to claim 5 wherein said statistical treatment is a technique comprising taking the second derivative of the absorbance spectrum.

7. The process of claim 5 wherein said statistical treatment is multiple linear regression analysis.

8. The process of claim 5 wherein said statistical treatment is partial least squares analysis.

9. The process according to claim 1 wherein said mixture flows substantially intermittently or continuously past the point of measuring said absorbance.

10. The process according to claim 1 wherein the hydrocarbon mixture is a pipelined crude oil.

11. The process according to claim 1 wherein the hydrocarbon mixture is a desalted crude oil.

12. The process according to claim 11 wherein said signal is used to control the severity of an atmospheric distillation column by adjusting temperature, throughput, and/or unit space velocity.

13. The process according to claim 1 wherein the hydrocarbon mixture is an atmospheric bottoms.

14. The process according to claim 13 wherein said signal is used to control the severity of a vacuum distillation column by adjusting cut point, temperature, throughput, and/or unit space velocity.

15. The process according to claim 1 wherein the hydrocarbon mixture is a vacuum bottoms.

16. The process according to claim 15 wherein said signal is used to control the severity of a solvent deasphalting unit by adjusting temperature, throughput, unit space velocity and/or alkane solvent to vacuum bottoms ratio.

17. The process according to claim 16 wherein said signal is used to control the severity of a visbreaker by adjusting temperature, throughput, and/or unit space velocity.

18. The process according to claim 1 wherein the hydrocarbon mixture is a solvent deasphalting product.

19. A process according to claim 1 wherein said signal is used to control at least one process selected from the group of:
   a. atmospheric distillation, whereby a bottoms product having a desired asphaltene concentration is produced, by adjusting throughput, temperature, or unit space velocity;
   b. vacuum distillation, whereby a bottoms product having a desired asphaltene concentration is produced, by adjusting temperature, throughput and/or unit space velocity;
   c. solvent deasphalting, whereby a deasphalted oil product having a desired asphaltene concentration is produced, by adjusting temperature, throughput, unit space velocity and/or alkane solvent to vacuum bottoms ratio; and
   d. visbreaking whereby a visbreaker product of desired asphaltene concentration is produced by adjusting temperature, throughput, and/or unit space velocity.

* * * * *